United States Patent [19]

Strebelle et al.

[11] Patent Number: 5,233,108
[45] Date of Patent: Aug. 3, 1993

[54] CATALYTIC HYDROCHLORINATION SYSTEM AND PROCESS FOR THE MANUFACTURE OF VINYL CHLORIDE FROM ACETYLENE AND HYDROGEN CHLORIDE IN THE PRESENCE OF THIS CATALYTIC SYSTEM

[75] Inventors: Michel Strebelle, Brussels; André Devos, Sint-Stevens-Woluwe, both of Belgium

[73] Assignee: Solvay (Société Anonyme), Brussels, Belgium

[21] Appl. No.: 900,933

[22] Filed: Jun. 18, 1992

[30] Foreign Application Priority Data

Jun. 20, 1991 [BE] Belgium .............................. 09100599

[51] Int. Cl.$^5$ .............................................. C07C 17/08
[52] U.S. Cl. ...................................... 570/233; 502/167
[58] Field of Search ......................................... 570/233

[56] References Cited

U.S. PATENT DOCUMENTS 4,912,271 3/1990 Thelen et al. .

FOREIGN PATENT DOCUMENTS

| 090443 | 5/1983 | European Pat. Off. . |
| 709000 | 8/1941 | Fed. Rep. of Germany . |
| 3500318 | 8/1985 | Fed. Rep. of Germany . |
| 237116 | 6/1979 | U.S.S.R. . |
| 2001546 | 7/1979 | United Kingdom . |

OTHER PUBLICATIONS

Abstract 00683A, Derwent Publications Ltd., Electro--Chemical IND KK, JA 52/136104.
Chemical Abstracts, vol. 71—12510v.

Primary Examiner—Howard T. Mars
Attorney, Agent, or Firm—Spencer, Frank & Schneider

[57] ABSTRACT

Catalytic system comprising at least one group VIII metal compound and at least one amine hydrochloride whose melting point is lower than or equal to 25° C. This catalytic system is suitable for the preparation of vinyl chloride by reacting acetylene with hydrogen chloride.

9 Claims, No Drawings

CATALYTIC HYDROCHLORINATION SYSTEM AND PROCESS FOR THE MANUFACTURE OF VINYL CHLORIDE FROM ACETYLENE AND HYDROGEN CHLORIDE IN THE PRESENCE OF THIS CATALYTIC SYSTEM

The present invention relates to a catalytic hydrochlorination system based on a group VIII metal compound and a process for the manufacture of vinyl chloride by hydrochlorination of acetylene in the presence of such a catalytic system.

The manufacture of vinyl chloride by reaction between acetylene and hydrogen chloride is commonly carried out in the gas phase, in a fixed bed reactor, in the presence of a heterogeneous solid catalyst based on mercury chloride on a support. Chiefly for reasons of toxicity, there currently exists a growing interest in catalytic systems which are free from mercury compounds. Various catalysts intended to replace the current catalysts in the gas phase processes have been developed. For example, the unexamined Japanese Patent Application 52/136104 describes a process for hydrochlorination of acetylene in the gas phase in the presence of a fixed bed of catalyst consisting of noble metal halides deposited on active charcoal. Hitherto, however, the lifetimes of such alternative catalysts intended for gas phase processes remain very much shorter than those of catalysts based on mercury compounds.

Moreover, the literature offers certain examples of hydrochlorination of acetylene in the presence of a liquid catalytic medium. German Patent 709,000 describes a process for the preparation of vinyl halides by bringing acetylene into contact, at high temperature, with a molten mass of hydrogen halide salts of organic bases enclosing a conventional catalyst. Aliphatic, aromatic or heterocyclic amines and their mixtures are envisaged as organic bases In Example 1, vinyl chloride is obtained by dispersion of hydrogen chloride and acetylene in a mixture consisting of 350 parts by volume of pyridine, 350 parts by volume of diethylamine and 100 parts by weight of mercury chloride, maintained at 220°-225° C. Author's certificate SU-237,116 describes the use of an acidic aqueous solution containing 46% by weight of cuprous chloride and from 14 to 16% by weight of a methyl-, dimethyl- or trimethylamine hydrochloride. Patent Application EP-A-0,340,416 discloses a process for the preparation of vinyl chloride by reaction of acetylene with hydrogen chloride in the presence of a palladium compound as catalyst in a solvent consisting of an aliphatic or cycloaliphatic amide, at a temperature higher than room temperature. Although it allows high yields to be achieved, this process has, nevertheless, certain significant disadvantages: it would appear that, under the reaction conditions, the liquid catalytic system progressively degrades, forming blackish products of carbonaceous appearance. Moreover, in the presence of hydrogen chloride, the amide is converted into the hydrochloride, whose melting point is generally much higher than room temperature. N-Methylpyrrolidone hydrochloride, for example, is liquid only above 80° C. In practice, that can cause serious problems in use, problems relating to phenomena of solidification of the catalytic mixture during reactor shutdowns or blockage of the pipework at the coldest places in the plant. The whole of the reactor as well as the pipework in which the reaction mixture circulates must consequently be held continuously at a temperature above the melting temperature of the hydrochloride.

Consequently, the objective of the invention is a catalytic hydrochlorination system which is free from mercury compounds, and stable and easy to use because it remains liquid at room temperature. Another objective of the invention is to provide a process for the synthesis of vinyl chloride by hydrochlorination of acetylene in the presence of such a catalytic system which does not degrade under the reaction conditions and which additionally makes it possible to obtain vinyl chloride with a selectivity greater than 99.9% and thus to greatly reduce the quantity of by-products to be removed. Unlike the systems based on mercury compounds, the catalytic system according to the invention has the further advantage of avoiding the vaporisation o metal salts in the plant.

The invention relates to a catalytic hydrochlorination system, more particularly for hydrochlorination of acetylene. This catalytic system comprises at least one group VIII metal compound and an amine hydrochloride whose melting point is lower than or equal to 25° C.

Amine hydrochlorides whose melting point is lower than or equal to 25° C. are especially the hydrochlorides of amines which are strongly sterically hindered, such as the hydrochlorides of amines corresponding to the following generic formula:

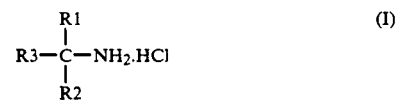

(I)

In this formula, R1 and R2 are hydrogen atoms or optionally identical alkyl or aryl groups and R3 is an alkyl or aryl group. R1 and R3 can optionally form together, by means of carbon atoms which connect them, a ring, for example of 5 or 6 carbon atoms, which can be substituted by alkyl groups. Preferably, R1, R2 and R3 are alkyl groups.

Alkyl group means any linear or branched carbon chain, optionally substituted by one or more aryl groups. Aryl group means any aromatic radical optionally substituted by one or more alkyl groups.

The total number of carbon atoms in this compound is at least equal to 8. It is preferably at least equal to 12. The total number of carbon atoms in this compound is generally at most equal to 30. It is preferably at most equal to 24.

Amine hydrochloride is meant to denote one or more amine hydrochlorides, including any mixture of hydrochlorides of several amines, for example, of several isomeric compounds. Such a mixture of hydrochlorides of several amines can also be used, especially by reason of its greater availability or of its lower cost in relation to the pure compounds. An example of such an amine hydrochloride comprising a mixture of various compounds corresponding to formula (I) is obtained by reacting hydrogen chloride with commercial products such as the primary tert-alkylamines Primene 81-R and Primene JM-T of Rohm and Haas Co, consisting of mixtures of $C_{12}$-$C_{14}$ and $C_{18}$-$C_{22}$ isomeric amines respectively. In certain cases, it can also prove advantageous to intentionally mix hydrochlorides of different amines because of the existence of eutectics between these compounds, which exhibit a melting point lower than that of each of the constituents.

Good results were obtained with a catalytic system comprising a tert-alkylamine hydrochloride (R1, R2 and R3 representing alkyl groups) containing from 10 to 25 carbon atoms such as the primary tert-alkylamines Primene 81-R and Primene JM-T of Rohm and Hass Co. Other amine hydrochlorides which have also given good results are the amine hydrochlorides in which R1 and R2 are hydrogen atoms and R3 is an aryl or alkyl group, for example the hydrochloride of polyisopropylbenzylamine and the hydrochloride of polyethyl-$\beta$-phenethylamine. Such highly sterically hindered amines can be easily obtained, for example, from the corresponding amines whose aromatic ring is nonalkylated-, —in the case of the compounds above, respectively from benzylamine and from 2-phenylethylamine —by protection of the amine function by reaction with a carboxylic acid anhydride, standard alkylation of the aromatic ring of the amide obtained and, finally, alkaline hydrolysis of the amide function.

The group VIII metal compounds used in the catalytic systems of the present invention are generally chosen from iron, cobalt, nickel, ruthenium, rhodium, palladium, osmium, iridium or platinum compounds or from their mixtures. The chlorides of these groups VIII metals are preferred, but any other compound which can be converted to chloride in the presence of hydrogen chloride during the preparation of the catalytic system can also be used. Preferably, the group VIII metal compound used in the present invention is chosen from platinum compounds and palladium compounds, such as platinum(II) chloride or palladium(II) chloride or a platinochloride or a palladochloride of alkali metals or of alkaline-earth metals—for example, $Na_2PtCl_4$, $Na_2PdCl_4$, $K_2PtCl_4$, $K_2PdCl_4$, $Li_2PtCl_4$, $Li_2PdCl_4$, $(NH_4)_2PtCl_4$ and $(NH_2)_2PdCl_4$ —, hexachloroplatinic acid or its salts, for example $Na_2PtCl_6$, $K_2PtCl_6$, $Li_2PtCl_6$, palladium compounds in which the palladium has a high valency, such as $Na_2PdCl_6$, $K_2PdCl_6$, $Li_2PdCl_6$, etc. It is also possible to use complexes of group VIII metals in which the metal is at 0 valency, such as the $Pt(P\phi_3)_2$, $Pd(P\phi_3)_2$, $(P\phi_3)Pt(CO)$, etc complexes.

Mixtures of group VIII metal compounds can also be used.

The group VIII metal compounds which are particularly preferred are platinum(II) chloride and palladium(II) chloride. When the catalytic system contains a tert-alkylamine hydrochloride (R1, R2 and R3 represent alkyl groups), the most particularly preferred group VIII metal compound is platinum(II) chloride. When the catalytic system contains an amine hydrochloride with R1 and/or R2 representing a hydrogen atom, the most particularly preferred group VIII metal compound is palladium(II) chloride.

The most particularly preferred catalytic system contains a tert-alkylamine hydrochloride, for example that obtained starting from the primary tert-alkylamine Primene 81-R, and platinum(II) chloride. Such a catalytic system makes it possible to synthesise vinyl chloride with a selectivity greater than 99.9%. Furthermore, this system shows virtually no degradation over time.

The content of group VIII metal compound in the catalytic system, expressed in millimoles per liter of amine hydrochloride is generally greater than or equal to approximately 1 mmol/l, preferably greater than or equal to approximately 10 mmol/l. The content of group VIII metal compound in the catalytic system is generally less than or equal to approximately 200 mmol/l, preferably less than or equal to approximately 100 mmol/l. Although it is not indispensable, it is nevertheless preferable that all the group VIII metal compound included in the catalytic system be in the dissolved form.

The invention also relates to a process for the manufacture of vinyl chloride by hydrochlorination of acetylene in the presence of a catalytic system comprising at least one group VIII metal compound and an amine hydrochloride whose melting point is lower than or equal to 25° C. The nature and the proportions of the constituents of the catalytic system used in the process according to the invention are those defined above.

In the process according to the invention, the catalytic system defined above can be used in the liquid phase. It can also be deposited on a solid support such as a silica, an alumina or an active charcoal, to the limit of the porous volume of the support. Preferably, the catalytic system is used in the liquid phase. However, the viscosity of this liquid at the reaction temperature often limits the efficiency of the exchange of materials between the gas phase which contains the reactants and the liquid phase in which the hydrochlorination reaction takes place. Consequently, the catalytic system is preferably diluted with an organic solvent. The choice of the nature of the organic solvent used in the process according to the invention is conditioned especially by the necessity that it should be inert with respect to the reactants under the reaction conditions, that it should be miscible with the amine hydrochloride and by the wish that it should form with this hydrochloride a mixture whose viscosity is lower than that of the hydrochloride alone. Moreover, for reasons of safety and of ease of use, preference is given to organic solvents which are not very volatile. The choice of the organic solvent is also influenced by its ability to absorb acetylene. Solvents which satisfy the various criteria set out above are chosen from aliphatic, cycloaliphatic and aromatic hydrocarbons and their mixtures, for example $C_7$ to $C_{15}$ paraffins and alkylbenzenes, especially xylenes, propylbenzenes, butylbenzenes or methylethylbenzenes. For reasons of an economic nature the solvent used is preferably chosen from commercial products consisting of mixtures of aliphatic hydrocarbons such as the Esso solvent Isopar or the Shell solvent Shellsol K or of mixtures of aromatic compounds such as the Esso solvent Solvesso or the Shell solvent Shellsol AB.

Solvents which have given good results are saturated aliphatic solvents, such as the solvent Shellsol K consisting of petroleum cuts which have a boiling point of between approximately 190° C. and approximately 250° C.

Other solvents which may be envisaged on the basis of the various criteria given above are certain heavy halogenated compounds such as haloalkanes, halobenzenes and other halogenated derivatives of aromatic compounds.

When the catalytic system is used in the liquid phase and when it is diluted with an organic solvent, the weight ratio of the solvent to the amine hydrochloride is generally greater than or equal to approximately 0.01. Preferably, this ratio is greater than or equal to approximately 0.05. Under the particularly preferred conditions, it is greater than or equal to approximately 0.2. This ratio is generally less than or equal to approximately 5. Preferably, it is less than or equal to approximately 3. Under the particularly preferred conditions, it is less than or equal to approximately 2.

The process according to the invention can be carried out from room temperature to approximately 220° C. At a higher temperature, the catalytic system has a tendency to rapidly degrade. The preferred reaction temperature, that is to say one which offers the best compromise between productivity, yield and stability of the catalytic medium is higher than or equal to approximately 80° C. The best results are obtained at temperatures higher than or equal to approximately 120° C. Preferably, the reaction temperature does not exceed approximately 200° C. A reaction temperature of less than or equal to approximately 170° C. is particularly preferred. The process according to the invention is generally carried out at atmospheric pressure or at a slightly greater pressure compatible with the safety regulations for the handling of acetylene, that is to say not exceeding approximately 1.5 bar.

The process for the manufacture of vinyl chloride by hydrochlorination of acetylene according to the invention is carried out by bringing the gaseous reagents—acetylene and hydrogen chloride—into contact with the catalytic system in any appropriate reactor.

When the catalytic system is used in the liquid phase, the process according to the invention can be carried out conventionally in any apparatus which promotes gas-liquid exchange, such as a plate column or a flooded column containing packing. Another method of use of the process which makes possible good exchange of material between the liquid and gaseous phases consists in using a counterflow reactor, optionally of the sprayed packing bed type, the liquid catalytic system trickling over the stacks, countercurrentwise to the gaseous flow of the reactants.

When the catalytic system is deposited on an appropriate solid support, it can advantageously replace the mercury catalysts in current plants operating with stationary bed reactors In the process according to the invention, the molar ratio of the hydrogen chloride to the acetylene introduced into the reactor is generally greater than or equal to approximately 0.5. Preferably, this ratio is greater than or equal to approximately 0.8. Generally, this molar ratio is less than or equal to approximately 3. Good results have been obtained with a molar ratio of the hydrogen chloride to the acetylene introduced into the reactor of less than or equal to approximately 1.5. The acetylene and the hydrogen chloride can be brought into contact inside the reactor or, preferably, mixed prior to their introduction into the reactor.

When working in liquid medium, with the aim of increasing the quantity of acetylene dissolved in the liquid phase, it is also possible to use a process in which only the acetylene is introduced into the reactor in gaseous form, where it reacts with the hydrogen chloride present in the liquid phase in the hydrochloride form, the amine hydrochloride of the catalytic system being regenerated by bringing a liquid shuttle containing the amine into contact with hydrogen chloride outside the reactor.

Generally, the catalytic system is prepared by dissolving or dispersing the required quantity of group VIII metal compound in the amine or in the amine/organic solvent mixture and then saturating this solution with hydrogen chloride, resulting in the formation of the amine hydrochloride. It is however also possible to first saturate the amine or the amine/organic solvent mixture with hydrogen chloride in order to form the amine hydrochloride and then to introduce the group VIII metal compound into the amine hydrochloride or into the mixture of the latter with the organic solvent afterwards. Usually, the quantity of group VIII metal compound used is such that, in the catalytic system, all the group VIII metal compound is found in the dissolved form. As an indication, the solubility of platinum(II) chloride in the mixture of equal parts by weight of the hydrochloride of the amine Primene 81-R and of the solvent Shellsol K exceeds 1 mol/l. It is also possible, however, to use a group VIII metal compound in a quantity or of a nature such that a fraction at least of this compound is present in the catalytic system in a dispersed solid form, without prejudicing the invention.

The invention is illustrated by the following examples. Examples 1 to 5, 7, 13 to 15 and 18 to 27 are carried out according to the invention. Examples 6(C), 8(C) to 12(C), 16(C) and 17(C) are carried out by way of comparison.

EXAMPLES 1 to 6(C)

The catalytic system is prepared from the amine Primene 81-R, from palladium chloride and optionally from the solvent Shellsol K.

The amine Primene 81-R is a primary tertalkylamine, commercially available from Rohm and Haas. It is a mixture of amines, in which the number of carbon atoms is from 12 to 14. The solvent Shellsol K, commercially available from Shell, consists of a mixture of hydrocarbons, essentially of an aliphatic nature. The solvent used in these examples has an initial boiling point of 193° C. and a final boiling point of 245° C.

The amine Primene 81-R is first mixed with variable quantities of solvent Shellsol K and then 4 g of palladium(II) chloride, i.e. 22.6 mmol, are introduced with stirring into a liter of solution. The catalytic system is then prepared by saturating the solution with gaseous hydrogen chloride.

The reaction between acetylene and hydrogen chloride is carried out in the following manner:

A pyrex reactor with an internal volume of 45 ml, equipped with a jacket in which a heat-transfer oil circulates and with a device for introducing the reagents which consists of a nozzle of sintered glass intended to ensure the dispersion of the gases in the liquid medium, is charged with 30 ml of a solution consisting of the amine Primene 81-R, palladium(II) chloride and, optionally, the solvent Shellsol K.

The solution is heated to 150° C. and a gaseous flow containing a mixture of hydrogen chloride and acetylene in a molar ratio $HCl/C_2H_2$ of 1.17 is introduced into the reactor. According to the tests, the residence time of the gases in the reactor, that is to say the ratio of the volume of the reactor to the volume flow rate of the reagents at the reaction temperature is 2.5 s or 4.9 s. The gaseous product leaving the reactor is analysed by gas phase chromatography. The only reaction products observed are vinyl chloride (VC) and 1-chloroprene (1CPr). The results are collated in Table I. The quantity of vinyl chloride produced is expressed in grams per hour per liter of catalytic system. The selectivity is defined as the molar ratio of the VC produced to the sum $[VC+(2\times 1CPr)]$.

TABLE I

| Ex. No. | Weight ratio amine Primene 81R solvent Shellsol K | Residence time (s) | VC produced ($g \cdot h^{-1} \cdot l^{-1}$) | Selectivity (%) | Comments |
|---|---|---|---|---|---|
| 1 | 100/0 | 2.5 | 44 | 91.7 | |
| 2 | 75/25 | 4.9 | 126 | 93.4 | |
| 3 | 60/40 | 4.9 | 122 | 92.7 | |
| 4 | 50/50 | 4.9 | 100 | 91.6 | |
| 5 | 25/75 | 4.9 | 47 | 90.6 | |
| 6(C) | 0/100 | 4.9 | 2 | n.d. | Degradation of the reaction medium |

EXAMPLES 7 TO 12(C)

Various catalytic systems are prepared in the same manner as in Example 4, (identical weight quantities of amine Primene 81-R and of solvent Shellsol K), but the palladium chloride is replaced by an identical molar quantity (22.6 mmol/l) of platinum(II) chloride, of copper(I) chloride, of copper(II) chloride, of zinc(II) chloride, of bismuth(III) chloride and of tin(II) chloride.

The reaction of hydrochlorination of acetylene is carried out under the same conditions as in Examples 2 to 6, except for the residence time, which is equal to 4.95 s. The results are collated in Table II.

TABLE II

| Example No. | Nature of the metal compound | VC produced ($g \cdot h^{-1} \cdot l^{-1}$) | Selectivity (%) | Comments |
|---|---|---|---|---|
| 7 | PtCl$_2$ | 270 | 100 | Total solubility |
| 8(C) | CuCl | 0 | n.d. | Total solubility |
| 9(C) | CuCl$_2$ | 0 | n.d. | Almost total solubility |
| 10(C) | ZnCl$_2$ | 3 | n.d. | Total solubility |
| 11(C) | BiCl$_3$ | 3 | n.d. | Partial solubility |
| 12(C) | SnCl$_2$ | 0.6 | n.d. | Partial solubility |

EXAMPLES 13 TO 17(C)

Various catalytic systems are prepared in the same manner as in Examples 4 or 7, with identical weight quantities of amine and of solvent Shellsol K, but the amine Primene 81-R is replaced by other nitrogen compounds. The amine Primene JM-T used in test 13 is a mixture of $C_{18}$-$C_{22}$ primary tert-alkylamines, also commercially available from Rohm and Haas.

The hydrochlorination reaction of acetylene is carried out under the same conditions of temperature and of reactant proportions as in Examples 4 and 7. In Examples 13 to 16 (C), the residence time is 4.9 s; it is 2.5 s in test 17 (C). The results are collated in Table III.

TABLE III

| Ex. No. | Nature of nitrogen compound | Nature of the metal compound | VC produced ($g \cdot h^{-1} \cdot l^{-1}$) | Selectivity (%) | Comments |
|---|---|---|---|---|---|
| 13 | amine Primene JM-T | PdCl$_2$ | 86 | 92.2 | |
| 14 | 1:3 mixture by weight of polyisopropylbenzyl-amine and of polyethyl-$\beta$-phenethylamine | PdCl$_2$ | 320 | 97.6 | |
| 15 | 1:1 mixture by weight of polyisopropylbenzyl-amine and of polyethyl-$\beta$-phenethylamine | PtCl$_2$ | 35 | 99 | |
| 16(C) | Dimethylformamide | PdCl$_2$ | 116 | 93.2 | Degradation of the reaction medium |
| 17(C) | N-methyl-pyrrolidone | PdCl$_2$ | 243 | 98.7 | catalytic system solid at temp. $\leq 80°$ C. |

EXAMPLES 18 TO 21 various catalytic systems are prepared in the same manner as in Example 7 (identical weight quantities of amine Primene 82-R of solvent Shellsol K), but with variable quantities of platinum(II) chloride.

The hydrochlorination reaction of acetylene is carried out under the same conditions as in Example 7. The results are collated in Table IV. The yield is defined as the molar ratio of the VC produced to the acetylene used.

TABLE IV

| Test No. | Concentration of PtCl$_2$ (mmol/l) | Yield (%) | VC produced ($g \cdot h^{-1} \cdot l^{-1}$) | Selectivity (%) |
|---|---|---|---|---|
| 18 | 11.3 | 18 | 110 | 99.2 |
| 19 | 15 | 27.5 | 167 | 99.8 |
| 20 | 22.6 | 43 | 262 | 99.9 |
| 21 | 45.1 | 77.3 | 471 | 99.9 |

EXAMPLES 22 TO 25

The catalytic system of Example 20 is used in a micropilot reactor, using the same principle as the reactor used in Examples 1 to 21, but consisting of a pyrex column 2 m in height and 2.54 cm in diameter, filled with packing of the Raschig ring type. It is charged with 500 ml of catalytic solution.

The hydrochlorination reaction of acetylene is carried out under the same operating conditions of temperature and of reactant proportions as in the preceding examples but with different residence times. The results are collated in Table V.

TABLE V

| Ex. No. | Residence Time (s) | Yield (%) | VC produced $(g \cdot h^{-1} \cdot l^{-1})$ | Selectivity (%) |
|---|---|---|---|---|
| 22 | 4.9 | 17.6 | 107 | 99.94 |
| 23 | 9.7 | 41 | 126 | 99.93 |
| 24 | 19.8 | 79.7 | 120 | 99.95 |
| 25 | 38.4 | 98.8 | 77 | 99.97 |

EXAMPLE 26

Various catalytic systems are prepared in the same manner as in Example 20 but the solvent Shellsol K is replaced by the solvent Solvesso 150. The solvent Solvesso 150, commercially available from Esso, consists of a mixture of hydrocarbons, essentially of aromatic (alkylbenzenes) nature, whose initial boiling point is 188° C. and whose final boiling point is 208° C. The hydrochlorination reaction of acetylene is carried out under the same conditions as in Example 20. The results are collated in Table VI.

TABLE VI

| Ex. No. | Residence Time (s) | Yield (%) | VC produced $(g \cdot h^{-1} \cdot l^{-1})$ | Selectivity (%) |
|---|---|---|---|---|
| 24 | 4.95 | 44.5 | 271 | 99.95 |

EXAMPLE 27

The catalytic system is prepared by impregnating 50 ml of an alruaina, dried beforehand for 24 hours at 250° C., with 19.4 ml of a solution of amine Primene 81-R containing 22.6 mmol of PtCl$_2$ per liter and then by passing a current of gaseous hydrogen chloride over the impregnated alumina placed in the reactor. The alumina used is an alumina Aluperl KC GS 2078/3 from Kali Chemie. Its characteristics are the following: beads 3 to 4 mm in diameter; BET specific surface area: 179$^2$/g; pore volume: 0.63 ml/g; specific weight: 0.71 g/ml; volume of water of absorption : 0.59 ml/g. A similar reactor is used to that used in Examples 1 to 21, but with an internal volume equal to 70 ml. The reactor is heated to 200° C. and a gas stream containing a mixture of hydrogen chloride and of acetylene with a molar ratio HCl/C$_2$H$_2$ of 1.17 is introduced into the reactor. The residence time of the gases is 7.5 s. The quantity of vinyl chloride produced is 32.2 grams per hour and per gram of platinum used. The selectivity of the reaction is 99.71%.

We claim:

1. Process for the manufacture of vinyl chloride by reacting acetylene with hydrogen chloride in the presense of a catalytic system, characterised in that the catalytic system comprises at least one group VIII metal compound and an amine hydrochloride whose melting point is lower than or equal to 25° C.

2. Process according to claim 1, characterised in that the amine hydrochloride corresponds to the formula

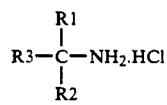

with R1 and R2 representing hydrogen atoms or optionally identica alkyl or aryl groups and R3 an alkyl or aryl group, the said amine hydrochloride containing from 8 to 30 carbon atoms.

3. Process according to any one of claim 1 characterised in that the group VIII metal compound is chosen from palladium compounds and platinum compounds.

4. Process according to any one of claim 1 characterised in that the content of group VIII metal compound expressed in millimoles per liter of amine hydrochloride is greater than or equal to approximately 1 mmol/l and less than or equal to approximately 200 mmol/l.

5. Process according to any one of claim 1 characterised in that the catalytic system is deposited on a solid support.

6. Process according to any one of claim 1 characterised in that the catalytic system is used in the liquid phase.

7. Process according to claim 6, characterised in that the catalytic system is diluted with an organic solvent chosen from aliphatic, cycloaliphatic and aromatic hydrocarbons and their mixtures and in that the weight ratio between the said solvent and the amine hydrochloride varies from approximately 0.01 to approximately 5.

8. Process according to any one of claim 1 characterised in that the reaction is carried out at a temperature from approximately 80° C. to approximately 200° C.

9. Process according to any one of claim 1 characterised in that the hydrogen chloride and the acetylene are used in a molar ratio of approximately 0.5 to approximately 3.

* * * * *